(12) United States Patent
Hasegawa et al.

(10) Patent No.: US 9,722,431 B2
(45) Date of Patent: Aug. 1, 2017

(54) SPECIMEN PROCESSING SYSTEM

(71) Applicant: HITACHI HIGH-TECHNOLOGIES CORPORATION, Tokyo (JP)

(72) Inventors: Nozomi Hasegawa, Tokyo (JP); Kuniaki Onizawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 194 days.

(21) Appl. No.: 14/760,800

(22) PCT Filed: Dec. 13, 2013

(86) PCT No.: PCT/JP2013/083409
§ 371 (c)(1),
(2) Date: Jul. 14, 2015

(87) PCT Pub. No.: WO2014/112259
PCT Pub. Date: Jul. 24, 2014

(65) Prior Publication Data
US 2015/0357824 A1    Dec. 10, 2015

(30) Foreign Application Priority Data

Jan. 15, 2013 (JP) ................................. 2013-004195

(51) Int. Cl.
*H02J 4/00* (2006.01)
*G01N 35/00* (2006.01)
(52) U.S. Cl.
CPC .......... *H02J 4/00* (2013.01); *G01N 35/00584* (2013.01); *Y10T 307/461* (2015.04)
(58) Field of Classification Search
CPC ..... H02J 4/00; G01N 35/0084; Y10T 307/461
(Continued)

(56) References Cited

U.S. PATENT DOCUMENTS

| 6,290,907 B1 | 9/2001 | Takahashi et al. |
| 2002/0016683 A1 | 2/2002 | Shiba et al. |

FOREIGN PATENT DOCUMENTS

| EP | 1 376 137 A2 | 1/2004 |
| EP | 2 645 108 A1 | 10/2013 |

(Continued)

OTHER PUBLICATIONS

International Search Report of PCT/JP2013/083409.
Extended European Search Report received in corresponding European Application No. 13871317.7 dated Jul. 20, 2016.

*Primary Examiner* — Robert Deberadinis
(74) *Attorney, Agent, or Firm* — Mattingly & Malur, PC

(57) ABSTRACT

In the specimen processing system in which each of a specimen input portion which inputs a specimen, a specimen processing portion which processes the specimen, a specimen recovery portion which recovers the processed specimen, and a specimen transporting line which transports the specimen between the specimen input portion, the specimen processing portion, and the specimen recovery portion, are connected to each other by a plurality of processing (analysis) units, the processing (analysis) unit is provided with a CPU that controls the operation, and provided with a mechanism control portion which receives an electric signal from the CPU and operates the mechanism parts in the processing unit, and the mechanism part control portion includes means which can supply and stop the power of one or more arbitrarily specified mechanism parts by the electric signal from the CPU.

9 Claims, 9 Drawing Sheets

(58) Field of Classification Search
USPC .......................................................... 307/31
See application file for complete search history.

(56) References Cited

FOREIGN PATENT DOCUMENTS

| | | |
|---|---|---|
| JP | 9-054095 A | 2/1997 |
| JP | 9-072911 A | 3/1997 |
| JP | 11-148940 A | 6/1999 |
| JP | 2004-028933 A | 1/2004 |
| JP | 2011-013112 A | 1/2011 |
| WO | 2012/070557 A1 | 5/2012 |

SPECIMEN PROCESSING SYSTEM

TECHNICAL FIELD

The present invention relates to an automatic analysis system and a specimen preprocessing system (both are collectively called a specimen processing system) which performs an analysis or preprocessing of a specimen sample, such as blood or urine, and particularly relates to a specimen processing system which connects a plurality of preprocessing units and analysis units to each other via a transporting system.

BACKGROUND ART

Examples of a specimen processing system for performing automatic analysis of a biosample, such as blood or urine, include a specimen preprocessing system which performs centrifugal separation or dispensing processing with respect to a specimen, such as blood or urine, collected for examination, or labelling processing, or an automatic analysis system which analyzes the specimen processed in the specimen preprocessing system. Since there are many types of processing and analyses, a specimen processing system, in which each type of processing is performed in separate processing (analysis) units, and each of the processing (analysis) units are connected to each other via a specimen transporting system which transports the specimen, is used.

In the specimen processing system, when maintenance or failure handling work is performed during an operation, exchange work or the like of a corresponding mechanism part is performed, but at a location where electricity is used for a motor or a sensor at the mechanism part, it is necessary to stop the power supply to the mechanism part in order to prevent a failure of an electric component due to the work in a conduction state. In this case, a worker stops the power supply of the specimen processing system and stops the operation of the entire specimen processing system, by a main power switch of the specimen processing system. However, when the operation of the entire specimen processing system is stopped as described above, processing of the specimen or an examination result report is delayed.

As means for solving the above-described problem, in PTL 1, an automatic analysis apparatus in which a plurality of analysis units are connected to each other by a transporting line, and which can cut off the power supply to each analysis unit is disclosed. In PTL 2, an automatic analysis apparatus which includes a plurality of mechanisms, and which is provided with a switching circuit that can stop the power supply to each certain mechanism part is disclosed.

CITATION LIST

Patent Literature

PTL 1: JP-A-2004-28933
PTL 2: JP-A-2011-13112

SUMMARY OF INVENTION

Technical Problem

The technology in PTL 1 can continue the operation of the entire automatic analysis apparatus since other analysis units or the transporting line can be used even when the power supply of some of the analysis units is blocked. However, during the maintenance or failure handling work, since the power supply of all of the analysis units which are necessary to be operated is stopped, the power supply to the mechanism parts which do not require maintenance or failure handling work is also stopped.

The technology in PTL 2 can stop the power supply to each mechanism unit of the automatic analysis apparatus, but cannot select a certain mechanism part and stop the power supply of only the mechanism part since the power supply of predetermined mechanism parts is stopped automatically and interlockingly.

An object of the present invention is to provide a specimen processing system which connects a plurality of preprocessing units and analysis units via a transporting line, and can supply and stop the power supply of one or more specified mechanism parts while continuing the operation.

Solution to Problem

A configuration of the present invention to achieve the above-described object is as follows.

In a specimen processing system in which each of a specimen input portion which inputs a specimen, a specimen processing portion which processes the specimen, a specimen recovery portion which recovers the processed specimen, and a specimen transporting line which transports the specimen between the specimen input portion, the specimen processing portion, and the specimen recovery portion are connected by a plurality of processing (analysis) units, the processing (analysis) units include a CPU which receives an electric signal from a control portion that controls the specimen processing system, and controls the processing (analysis) units, and a mechanism control portion which receives the electric signal from the CPU, and operates mechanism parts in the processing units.

The mechanism control portion includes means which can supply and stop the power supply to a certain mechanism part by the electric signal from the CPU.

The specimen processing system may be a system in which the processing unit and the analysis unit are mixed with one another, in addition to a configuration in which only the specimen preprocessing unit is provided, and a configuration in which only the specimen analysis unit is provided.

The specimen processing portion means a unit which performs any of preprocessing of the specimen and analysis processing of the specimen. The specimen is stored in a specimen container, and transported on the specimen transporting line. However, regarding the transporting of the specimen, any of a method of transporting a specimen container itself, a method of transporting a specimen holder which holds one specimen container, and a method of transporting a specimen rack which holds a plurality of specimen containers, may be employed.

Advantageous Effects of Invention

According to the present invention, in the specimen processing system which is provided with a plurality of processing (analysis) units, by supplying or stopping the power of only one or more arbitrarily specified mechanism parts, an operation of the specimen processing system is possible while performing maintenance or failure handling work.

DESCRIPTION OF EMBODIMENTS

Hereinafter, an example of a system of the present invention will be described by using an example illustrated in FIG. 1.

Figure 1:
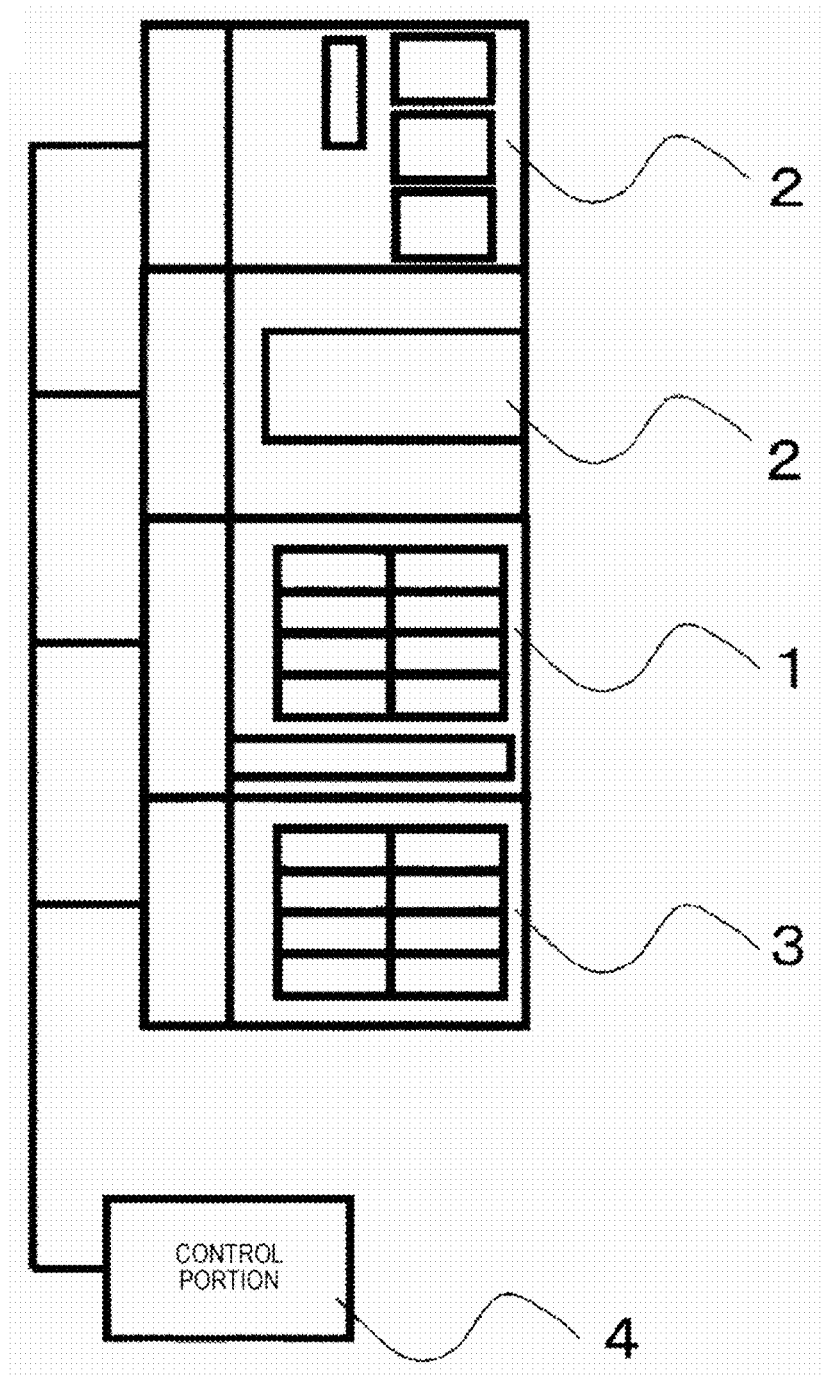
FIG. 1 is a schematic view illustrating an example of a system of the present invention.

FIG. 1 is a preprocessing unit of a specimen processing system which includes a specimen input portion 1 which inputs a test tube having a specimen sample, such as blood or urine, therein into a transporting line; a specimen processing portion 2 which performs preprocessing of a specimen, such as centrifugal separating processing of the specimen sample, such as blood or urine, plugging and unplugging processing of the test tube having the specimen sample, such as blood or urine, therein, label pasting processing with respect to the test tube for subdividing the specimen sample, such as blood or urine, or dispensing processing of the specimen sample, such as blood or urine; a specimen recovery portion 3 which classifies or accommodates the processed test tube; and a control portion 4 which controls these portions.

Figure 2:
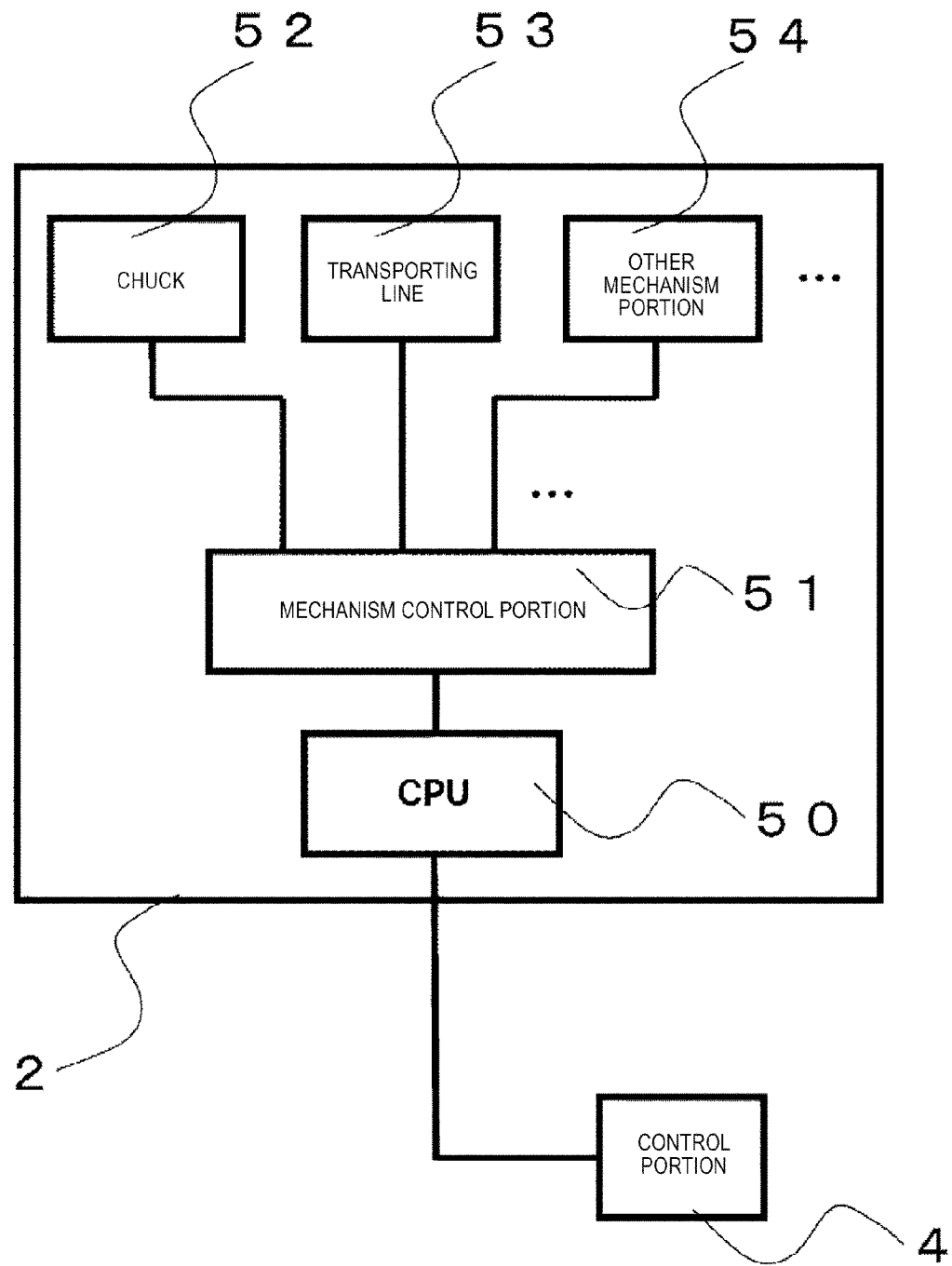
FIG. 2 is a schematic view illustrating an embodiment of the present invention.

A configuration of the general specimen processing portion 2 will be described by using an example illustrated in FIG. 2. FIG. 2 is a schematic block diagram of a certain specimen processing portion 2 in which a mechanism control portion 51 is connected to a chuck 52, a transporting line 53, and other mechanism portion 54, a CPU 50 is connected to the mechanism control portion 51, and the control portion 4 is connected to the CPU 50. In addition, a configuration of the specimen processing portion 2 is not limited to the configuration in FIG. 2.

Here, the chuck 52 is a mechanism for grabbing and moving a specimen container to another location, or for fixing the specimen or the test tube for performing some processing, and is a mechanism which is provided not only in the specimen processing portion, but also in the specimen input portion or the specimen recovery portion. For example, in a case of the specimen processing portion which performs the centrifugal separation processing, the chuck grabs the specimen which is transported through the transporting line, and transfers the specimen into an adapter or a bucket for centrifugal separation. In addition, in case of the specimen processing portion which performs plugging and unplugging processing, the chuck 52 is used for fixing the test tube during the plugging and unplugging processing.

The transporting line is provided for every specimen processing portion, and constitutes a transporting system across the entire specimen processing system as an end portion thereof is connected to the transporting line of the adjacent specimen processing portion. The specimen is transported to a desired unit by the transporting line.

As will be described later, examples of the other mechanism portion 54 include a specimen input mechanism, a centrifugal separating mechanism, an unplugging mechanism, a plug disposal mechanism, a label issuing mechanism, a label pasting mechanism, a dispensing head mechanism, a dispensing head moving mechanism, a plugging mechanism, a plug supply mechanism for plugging, and a specimen recovery mechanism.

In addition, a mechanism in the present invention means a configuration for realizing one function. For example, the chuck 52 is a configuration for realizing a function of grabbing the specimen container, and is one mechanism. In addition, the transporting line 53 is a configuration for realizing a function of transporting the specimen container, and is one mechanism.

The mechanism control portion 51 will be described by using an example illustrated in FIG. 3.

Figure 3:
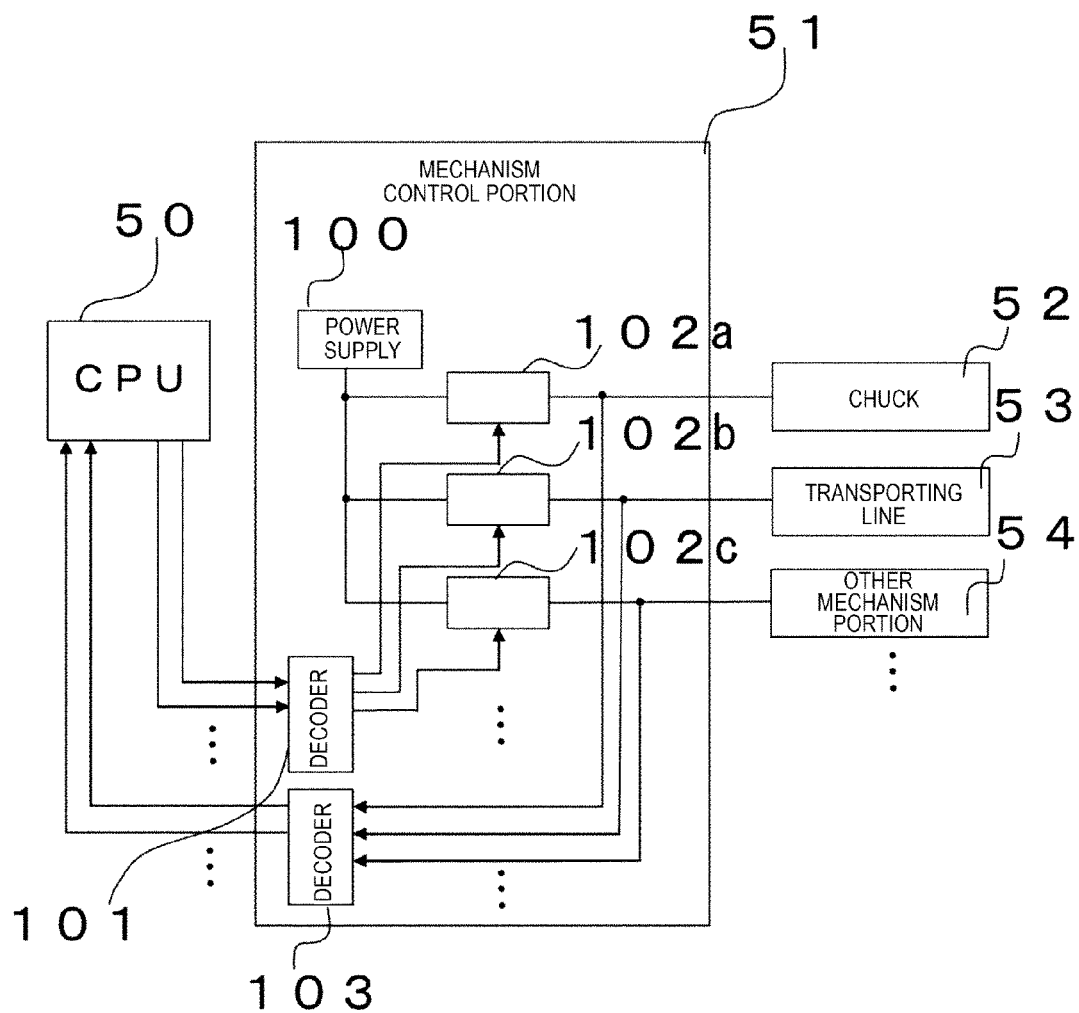
FIG. 3 is a schematic view illustrating the embodiment of the present invention.

FIG. 3 is a schematic example of the mechanism control portion 51, a power supply 100 which supplies power to the chuck 52, the transporting line 53, and the other mechanism portion 54 supplies the power to the chuck 52, the transporting line 53, and the other mechanism portion 54 through power switching portions 102a, 102b, and 102c which can open and close a circuit. When the circuits of the power switching portions 102a, 102b, and 102c are closed, the power supply 100 supplies the power to the chuck 52, the transporting line 53, and the other mechanism portion 54, and when the circuits of the power switching portions 102a, 102b, and 102c are opened, the power supply 100 stops supplying the power to the chuck 52, the transporting line 53, and the other mechanism portion 54. Opening and closing of the circuits of the power switching portions 102a, 102b, and 102c is possible by an output of an electric signal output by a decoder 101 which is controlled by an electric signal output by the CPU 50. By changing the electric signal output by the decoder 101 by combining the electric signal output by the decoder 101 with the electric signal output by the CPU 50, it is possible to open and close the circuit and to supply or stop the power supply 100 only with respect to the power switching portion 102a, and it is possible to open and close the circuit and to supply or stop the power supply 100 with respect to a free combination of the power switching portion 102a or the power switching portion 102b. It is possible to detect opening and closing of the power switching portions 102a, 102b, and 102c as input portions of a decoder 103 are respectively connected to the chuck 52, the transporting line 53, and the other mechanism portion 54 in parallel, the electric signal input to the decoder 103 changes by the opening and closing of the power switching portions 102a, 102b, and 102c, and the electric signal output to the CPU 50 changes.

Figure 4:
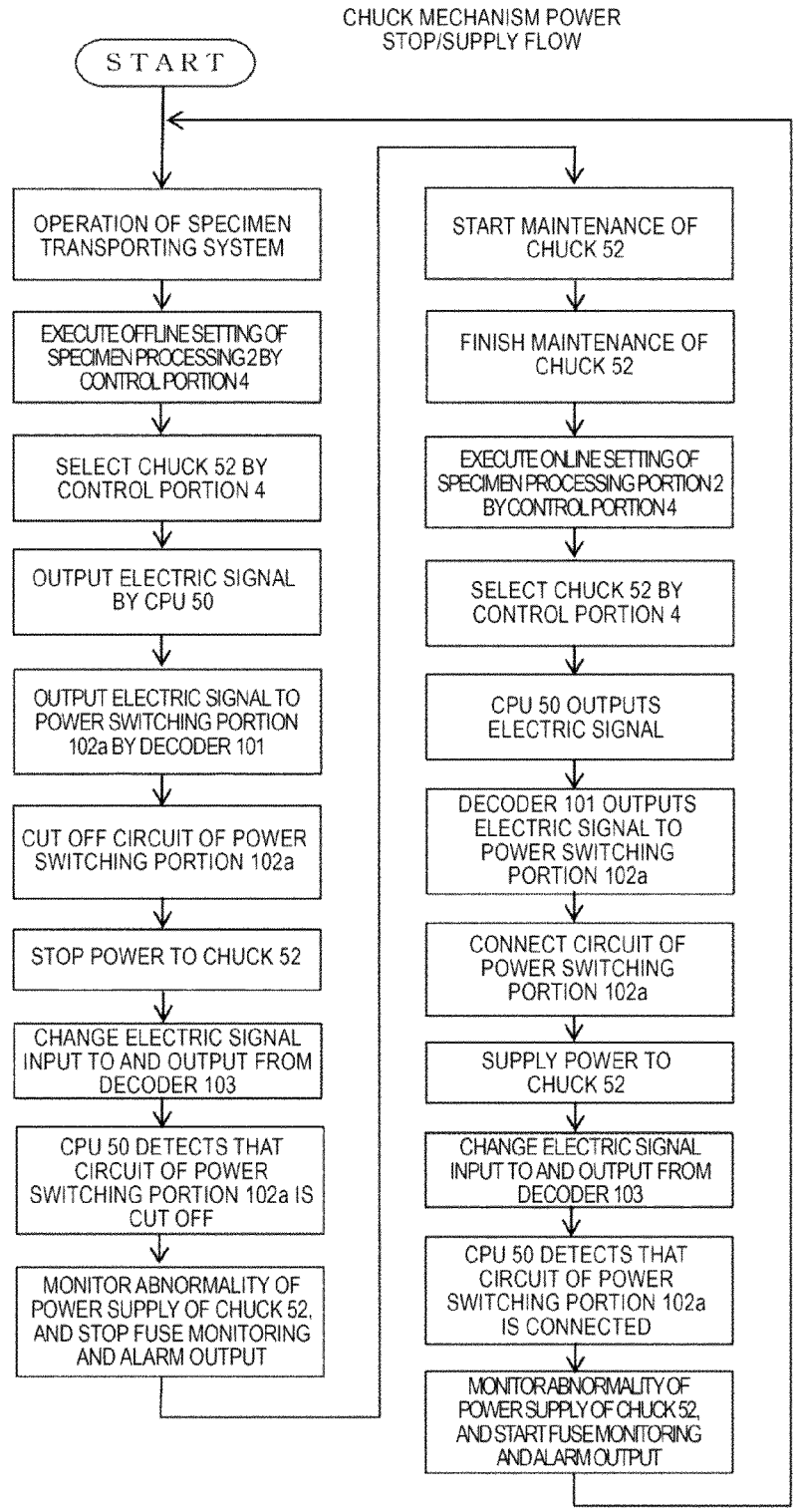
FIG. 4 is a view illustrating a flow of stopping power supply of a chuck mechanism in the embodiment of the present invention.

FIG. 4 illustrates a power stop/supply flow of the chuck 52 as an example.

During the operation of the specimen processing system, when performing offline setting of the specimen processing portion 2 by the control portion 4, it is possible to perform a power stop operation of the chuck 52, the transporting line 53, and the other mechanism portion 54 in the specimen processing portion 2.

Next, when the chuck 52 is selected by the operation portion 4, the electric signal is output to the decoder 101 through the CPU 50 by the operation portion 4, and the decoder 101 which receives the electric signal outputs the electric signal to the power switching portion 102a, and cuts off the circuit of the power switching portion 102a. Accordingly, the supply of the power supply 100 to the chuck 52 is stopped, the electric signal input to and output from the decoder 103 changes, and the CPU 50 detects that the circuit of the power switching portion 102a is cut off. After this, the operation portion 4 monitors abnormality of the power supply of the chuck 52, fuse monitoring and alarm output are stopped, and a state where maintenance is possible is achieved.

After finishing the maintenance, it is possible to perform a power supply operation of the chuck 52 in the specimen processing portion 2 when the online setting of the specimen processing portion 2 is performed, by the control portion 4.

In addition, when the chuck 52 is selected by the operation portion 4, the electric signal is output to the decoder 101 through the CPU 50 by the operation portion 4, and the decoder 101 which receives the electric signal outputs the electric signal to the power switching portion 102a, and connects the circuit of the power switching portion 102a. Accordingly, the supply of the power supply 100 to the chuck 52 is started, the electric signal input to and output from the decoder 103 changes, and the CPU 50 detects the connection of the circuit of the power switching portion 102a. After this, the operation portion 4 monitors abnormality of the power supply of the chuck 52, fuse monitoring and alarm output is started, and the specimen processing system returns to the operation.

Figure 5:
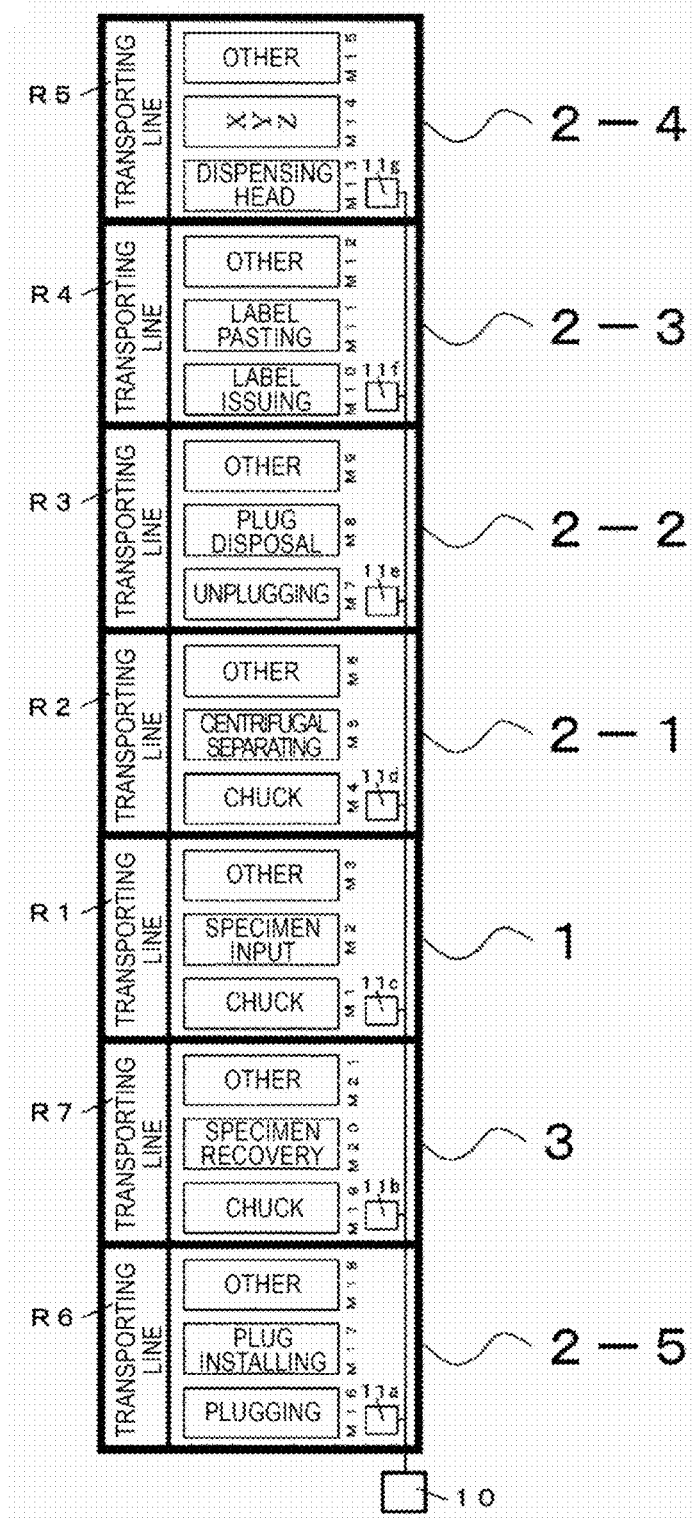
FIG. 5 is a schematic view illustrating an example of the system of the present invention.

FIG. 5 illustrates a block diagram of an example of the specimen processing system of the present invention. In addition, FIGS. 6 to 9 illustrate examples of each unit which constitutes the specimen processing system of FIG. 5.

In the specimen processing system, the specimen which is input from the specimen input portion 1 reaches the specimen recovery portion 3 via the specimen processing portion 2 (a centrifugal separation unit 2-1, a plugging unit 2-2, a label pasting unit 2-3, a dispensing unit 2-4, and an unplugging unit 2-5). In addition, the specimen input portion 1 and the specimen recovery portion 3 are positioned at the third and the second positions from the left of the specimen processing system, and the specimen is transported so as to draw a loop via transporting lines R1 to R7.

The specimen input portion 1 is provided with four mechanism portions, including a chuck mechanism M1, a specimen input mechanism M2, other mechanism M3, and the transporting line R1. The specimen processing portion 2 (the centrifugal separating unit 2-1, the plugging unit 2-2, the label pasting unit 2-3, the dispensing unit 2-4, and the unplugging unit 2-5) is provided with a chuck mechanism M4, a centrifugal separation mechanism M5, other mechanism M6, a transporting line R2, an unplugging mechanism M7, a plug disposal mechanism M8, other mechanism M9, a transporting line R3, a label issuing mechanism M10, a label pasting mechanism M11, other mechanism M12, a transporting line R4, a dispensing head mechanism M13, an XYZ mechanism M14, other mechanism M15, a plugging mechanism M16, a plug installing mechanism M17, other mechanism M18, and a transporting line R6. The specimen recovery portion 3 is provided with mechanism parts, such as a chuck mechanism M19, a specimen accommodation mechanism M20, other mechanism M21, and a transporting line R7.

In a system configuration in the related art, the supply of the power to each unit is performed through a power switch 10, and power switches 11a to 11g. In this case, when maintenance or exchange work of the chuck mechanism M4 is performed during the operation, in order to stop the power supply to the chuck mechanism M4, it is necessary to cut off the circuit by the power switch 11d, or to cut off the circuit by the main power switch 10. However, when the circuit is cut off by the power switch 11d, the power supply of the mechanism parts, such as the centrifugal separation mechanism M5, the other mechanism M6, and the transporting line R2, is stopped, processing by the centrifugal separation mechanism M5 or delivering of the specimen between the transporting lines R1 and R3 is not possible, and processing of the entire specimen processing system is delayed. In addition, when the circuit is cut off by the main power switch 10, since the power supply of all three mechanism parts, such as the specimen input portion 1, the specimen processing portion 2, and the specimen recovery portion 3, is cut off, the operation of the specimen processing system is stopped.

Meanwhile, as illustrated in FIG. 3, when a power switching portion 102 is provided with respect to each mechanism, it is possible to cut off the power supply of only the chuck mechanism M4 without stopping the centrifugal separation mechanism M5, the other mechanism M6, and the transporting line R2 of the specimen processing portion 2. For this reason, the transporting of the specimen between the transporting lines R1 and R3 or the centrifugal separation processing which is being executed is possible, and it is possible to reduce the delay of the processing.

In addition, when the specimen processing portion is provided with a plurality of chuck mechanisms M4 in one unit, it is possible to only stop the power supply to the chuck mechanism M4 which requires maintenance, and to continue the power supply to the other chuck mechanism M4. A processing performance of the chuck M4 deteriorates, but the operation of the entire specimen processing system can continue. In this manner, at the mechanism parts M1 to M21, when a plurality of the same type of mechanisms are provided in the same unit, it is possible to stop the power supply of only a certain mechanism, and to continue the power supply to other mechanisms. For this reason, even when the processing performance deteriorates, it is possible to continue the operation of the entire specimen processing system, and to reduce the delay of the processing.

In addition, when the power supply of the plugging mechanism M16 of the specimen processing portion 2 is stopped, the processing by the plugging mechanism M16 is stopped, but the transporting line R6 supplies the power. For this reason, it is possible to accommodate the specimen in the specimen accommodation mechanism M20 of the specimen recovery portion 3 through the transporting lines R6 and R7. In addition, after finishing the maintenance or the like, and restarting the supply of the power of the plugging M16, the specimen can be processed in the plugging mechanism M16 through the transporting lines R7 and R6.

In addition, when the power supply of the transporting line R4 of the specimen processing portion 2 is stopped, the power is supplied to the label issuing mechanism M10 and the label pasting mechanism M11. For this reason, it is possible to continue the processing, and to continue the processing of label issuing and pasting with respect to the specimen which is already transported.

Figure 6:
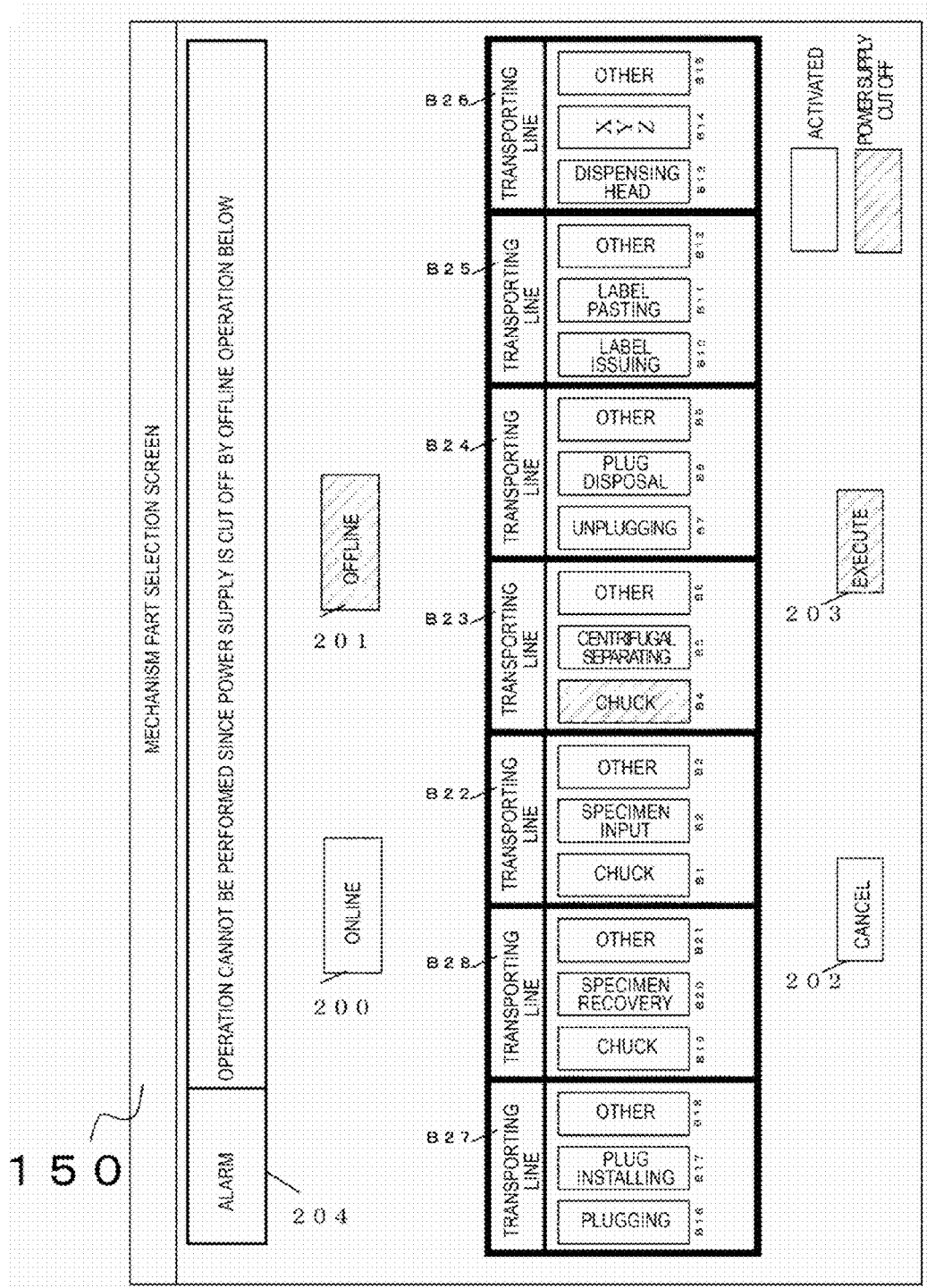
FIG. 6 is a schematic view illustrating the embodiment of the present invention.
Figure 7:
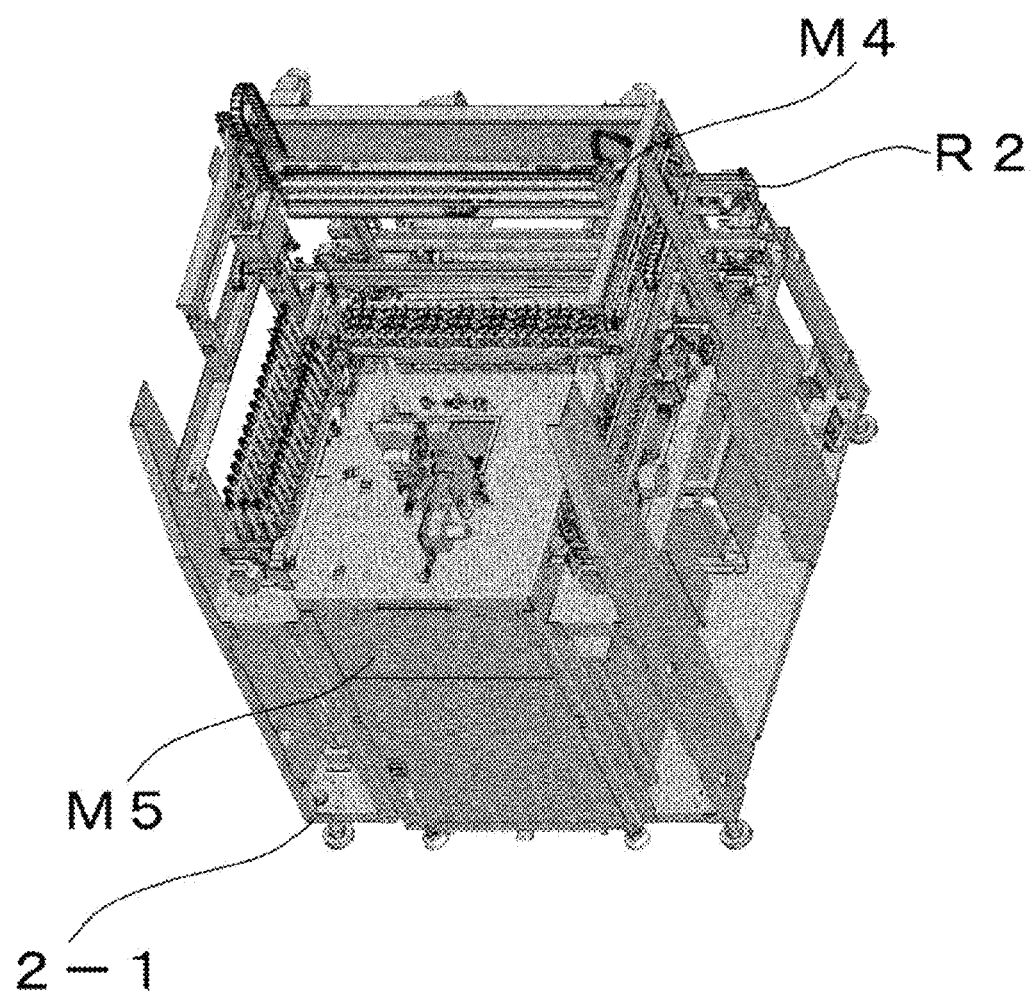
FIG. 7 is a schematic view illustrating an example of the system of the present invention.
Figure 8:
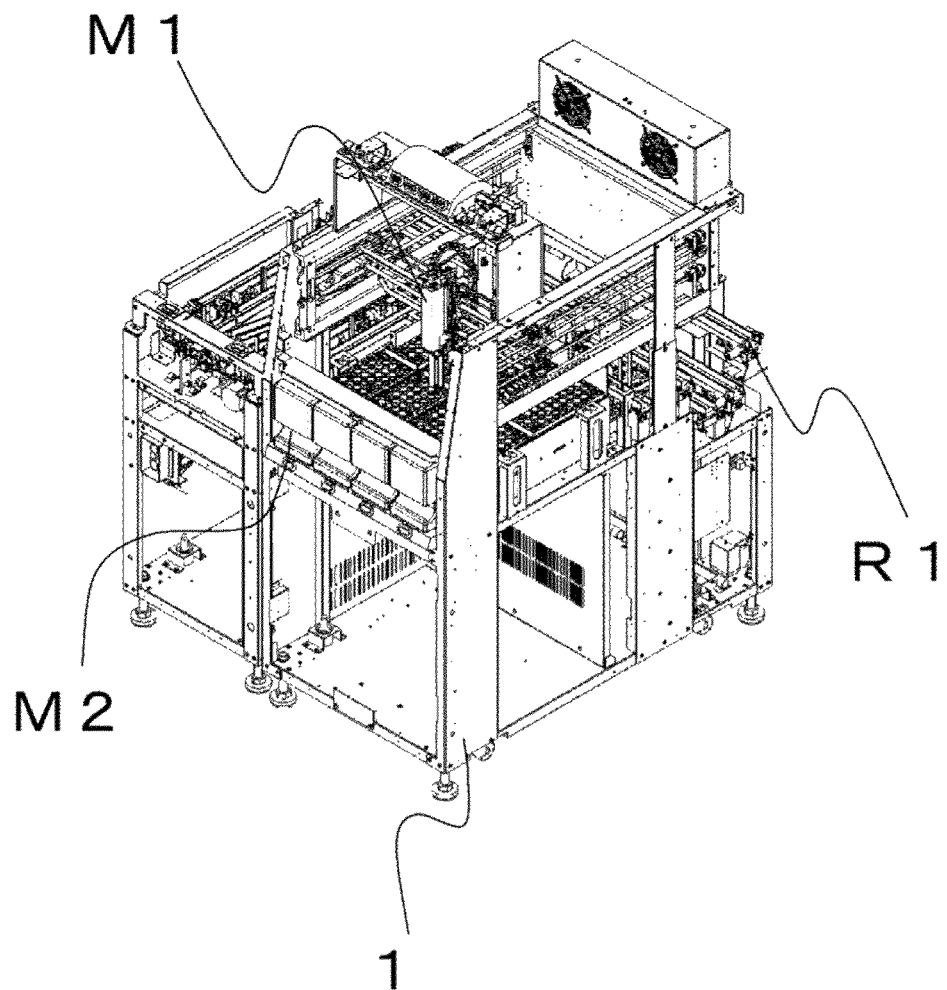
FIG. 8 is a schematic view illustrating an example of the system of the present invention.
Figure 9:
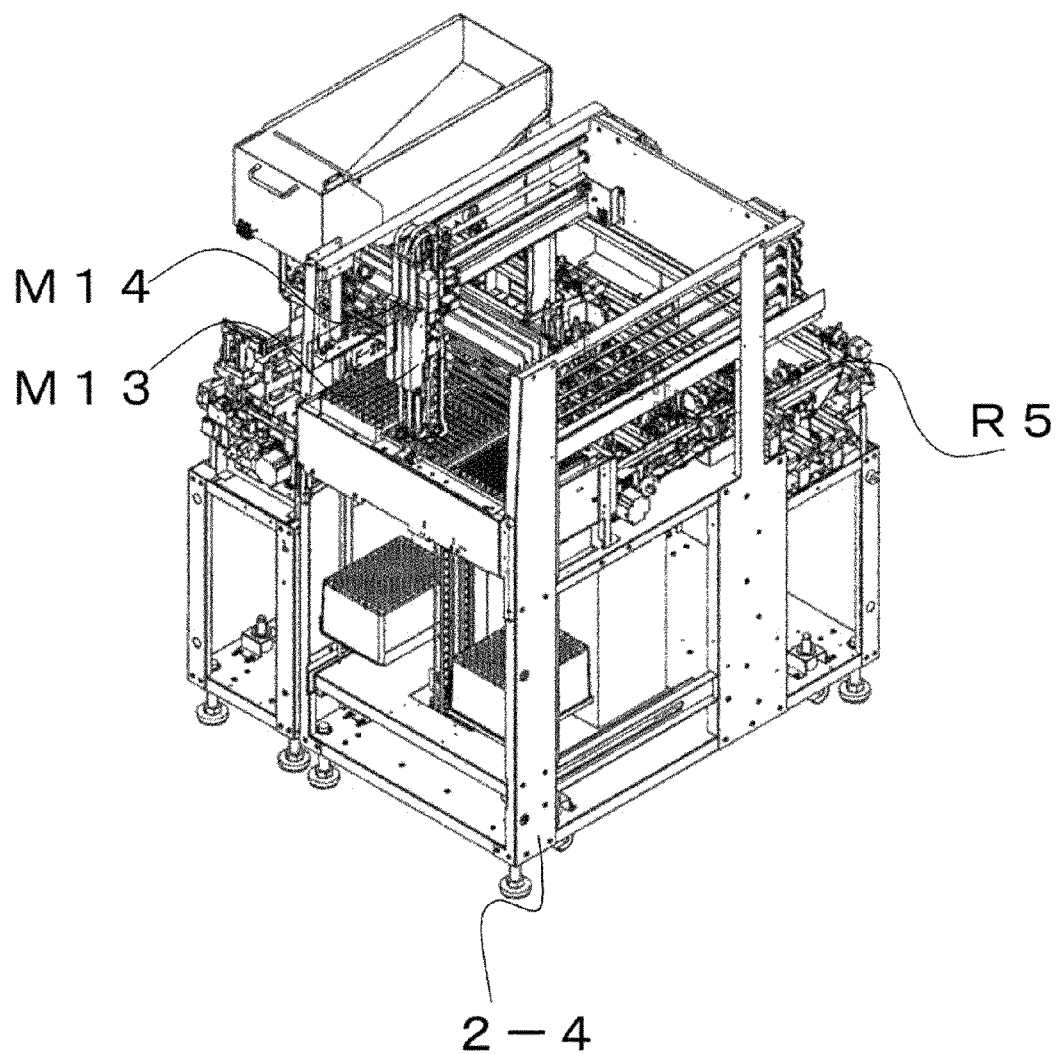
FIG. 9 is a schematic view illustrating an example of the system of the present invention.

FIG. 6 illustrates a mechanism part selection screen 150 of the specimen processing portion.

The control portion 4 is, for example, a computer for control, and is provided with an input device, such as a keyboard, a mouse, or a touch panel, and a display device, such as a liquid crystal display or a CRT. On the screen of the display device, the mechanism part selection screen 150 is displayed. On the mechanism part selection screen 150, a mechanism which can turn the power supply to each specimen processing portion ON/OFF is displayed as buttons B1 to B21. For example, a touch button B1 for selecting a mechanism part to which the power is stopped or supplied, a specimen input button B2, other button B3, a chuck button B4, a centrifugal separation button B5, other button B6, an unplugging button B7, a plug disposal button B5, other button B9, a label issuing button B10, a label pasting button B11, other button B12, a dispensing head button B13, an XYZ button B14, other button B15, a plugging button B16, a plug installing B17, other button B18, a chuck B19, a specimen recovery B20, and other button B21, correspond to the buttons B1 to B21.

As the other buttons, an offline button 200, an online button 201, a cancel button 202, and an execute button 203 are provided. In the mechanism part selection screen 150, an alarm output screen 204 which outputs an alarm during the offline operation is provided.

After selecting the chuck button B4 on the mechanism part selection screen 150, when the offline button 200 is pressed down and the execute button 203 is pressed down, the offline setting of the specimen processing portion 2 is performed, and the power supply to the chuck mechanism M4 is stopped. In order to only stop the power supply of the chuck mechanism M4, the power is supplied to the other specimen processing portion 2, the specimen input portion 1, and the specimen recovery portion 3, and while the specimen processing system continues the operation in mechanisms other than the chuck mechanism M4, it is possible to perform maintenance work or failure handling work of the chuck mechanism M4. After finishing the work, by pressing down the online button 201, and pressing down the execute button 203, the power supply to the chuck mechanism M4 of the specimen processing portion 2 is restarted. When cancelling the operation, it is possible to release the selection by pressing down the cancel button 202. After stopping the power supply in offline setting, when there is an operation indication with respect to a mechanism part to which the power supply is stopped, "operation cannot be performed since power supply is cut off by offline operation below" is output on the alarm output screen 204.

Since it is possible to stop and restart the power supply to an arbitrarily specified mechanism by the mechanism control portion 51 by the mechanism part selection screen 150, it is possible to perform operation confirm work while continuing the operation. In addition, in the specimen processing portion 2, when only the dispensing head button B13 is specified and the offline button 201 and the execute button 203 are pressed down, the dispensing processing is stopped. However, since the other mechanisms of the specimen processing portion 2 operate, for example, it is possible to respond to the next processing, such as label pasting, and it is also possible to prevent the delay of the processing even in a case of a specimen of which dispensing is already finished or a specimen which does not require dispensing.

The power switching portion 102 of the mechanism control portion 51 can only be provided at locations where electricity is used, such as a plurality of motors or sensors, and which are provided with the specimen input portion 1, the specimen processing portion 2, and the specimen recovery portion 3.

By combining these power switching portions, it is possible to realize an ON/OFF state of the power supply of the entire mechanism. In addition, in the example, as the specimen processing portion 2, a centrifugal separating unit or the like which performs the preprocessing with respect to the specimen is described, but for example, an analysis unit which performs analysis of the specimen may be employed.

REFERENCE SIGNS LIST

1 SPECIMEN INPUT PORTION
2 SPECIMEN PROCESSING PORTION
3 SPECIMEN RECOVERY PORTION
4 CONTROL PORTION
10 MAIN POWER SWITCH
11a to 11g POWER SWITCH
50 CPU
51 MECHANISM CONTROL PORTION
52 CHUCK
53 TRANSPORTING LINE
54 OTHER MECHANISM PORTION
100 POWER SUPPLY
101 DECODER
102a to 102c POWER SWITCHING PORTION
103 DECODER
150 MECHANISM PART SELECTION SCREEN
200 OFFLINE BUTTON
201 ONLINE BUTTON
202 CANCEL BUTTON
203 EXECUTE BUTTON
204 ALARM SCREEN
M1 CHUCK MECHANISM
M2 SPECIMEN INPUT MECHANISM
M3 OTHER MECHANISM
M4 CHUCK MECHANISM
M5 CENTRIFUGAL SEPARATION MECHANISM
M6 OTHER MECHANISM
M7 UNPLUGGING MECHANISM
M8 PLUG DISPOSAL MECHANISM
M9 OTHER MECHANISM
M10 LABEL ISSUING MECHANISM
M11 LABEL PASTING MECHANISM
M12 OTHER MECHANISM
M13 DISPENSING HEAD MECHANISM
M14 XYZ MECHANISM
M15 OTHER MECHANISM
M16 PLUGGING MECHANISM
M17 PLUG INSTALLING MECHANISM
M18 OTHER MECHANISM
M19 CHUCK MECHANISM
M20 SPECIMEN RECOVERY MECHANISM
M21 OTHER MECHANISM
R1 to R6 TRANSPORTING LINE
B1 CHUCK BUTTON
B2 SPECIMEN INPUT BUTTON
B3 OTHER BUTTON
B4 CHUCK BUTTON
B5 CENTRIFUGAL SEPARATION BUTTON
B6 OTHER BUTTON
B7 UNPLUGGING BUTTON
B8 PLUG DISPOSAL BUTTON
B9 OTHER BUTTON
B10 LABEL ISSUING BUTTON
B11 LABEL PASTING BUTTON
B12 OTHER BUTTON
B13 DISPENSING HEAD BUTTON
B14 XYZ BUTTON
B15 OTHER BUTTON
B16 PLUGGING BUTTON
B17 PLUG INSTALLING BUTTON
B18 OTHER BUTTON
B19 CHUCK BUTTON

B20 SPECIMEN RECOVERY BUTTON
B21 OTHER BUTTON
B22 TO B27 TRANSPORTING LINE BUTTON

The invention claimed is:

1. A specimen processing apparatus which is provided with a plurality of mechanisms each of which has one function, and processes a specimen, the apparatus comprising:
 a power supply which supplies electricity to the plurality of mechanisms that constitute the specimen processing apparatus;
 a circuit coupling the power supply to each mechanism of the plurality of mechanisms to provide a supply of the electricity from the power supply;
 indicating means for indicating a stop of the supply of the electricity to an arbitrary mechanism among the plurality of mechanisms; and
 a power switching portion that physically opens and closes the circuit to switch between supplying and stopping, respectively, the supply of the electricity to the arbitrary mechanism indicated by the indicating means.

2. The specimen processing apparatus according to claim 1, wherein
 the power switching portion switches the supplying and the stopping of the electricity to each of the mechanisms that uses the electricity.

3. The specimen processing apparatus according to claim 1, further comprising:
 a display device which displays the indicating means on a screen.

4. The specimen processing apparatus according to claim 1, wherein the specimen processing apparatus includes at least one of:
 a centrifugal separation unit which performs centrifugal separation processing of the specimen,
 an unplugging unit which performs unplugging processing of the specimen,
 a labelling unit which pastes a barcode label issued to the specimen,
 a dispensing unit which dispenses the specimen to a specimen container, or
 a plugging unit which performs plugging processing to the specimen.

5. The specimen processing apparatus according to claim 1, further comprising:
 a control device configured to monitor the arbitrary mechanism indicated by the indicating means, and control starting and stopping of an alarm output, based at least in part on an indication by the indicating means.

6. A specimen processing system comprising:
 a specimen processing unit which is provided with a plurality of mechanisms, each of which has one function, and processes a specimen;
 a transporting line which transports the specimen to the specimen processing unit;
 a power supply which supplies electricity to the plurality of mechanisms and the transporting line;
 a circuit coupling the power supply to the plurality of mechanism and the transporting line to provide a supply of the electricity from the power supply;
 indicating means for indicating a stop of the supply of the electricity to an arbitrary mechanism among the plurality of mechanisms; and
 a power switching portion that physically opens and closes the circuit to switch between supplying and stopping, respectively, the supply of the electricity to the arbitrary mechanism indicated by the indicating means.

7. The specimen processing system according to claim 6, further comprising:
 a specimen input unit which inputs the specimen to the specimen processing system; and
 a specimen recovery unit which recovers the specimen following completion of processing in the specimen processing system,
 wherein, with respect to the specimen input unit and the specimen recovery unit, the power switching portion switches the supplying and the stopping of the supply of the electricity to each mechanism having the specimen input unit and the specimen recovery unit.

8. The specimen processing system according to claim 6, further comprising:
 a control device configured to monitor the arbitrary mechanism indicated by the indicating means, and control starting and stopping of an alarm output, based at least in part on an indication by the indicating means.

9. A control device which controls an operation of a specimen processing apparatus including a plurality of mechanisms that process a specimen, the device comprising:
 a display device which displays an indicating screen for indicating supplying and stopping of electricity to an arbitrary mechanism of the plurality of mechanisms by physically opening and closing a circuit that supplies the electricity to the arbitrary mechanism.

* * * * *